Oct. 3, 1961 D. H. MOREY, JR Plant Pat. 2,097
ROSE PLANT
Filed Nov. 25, 1960
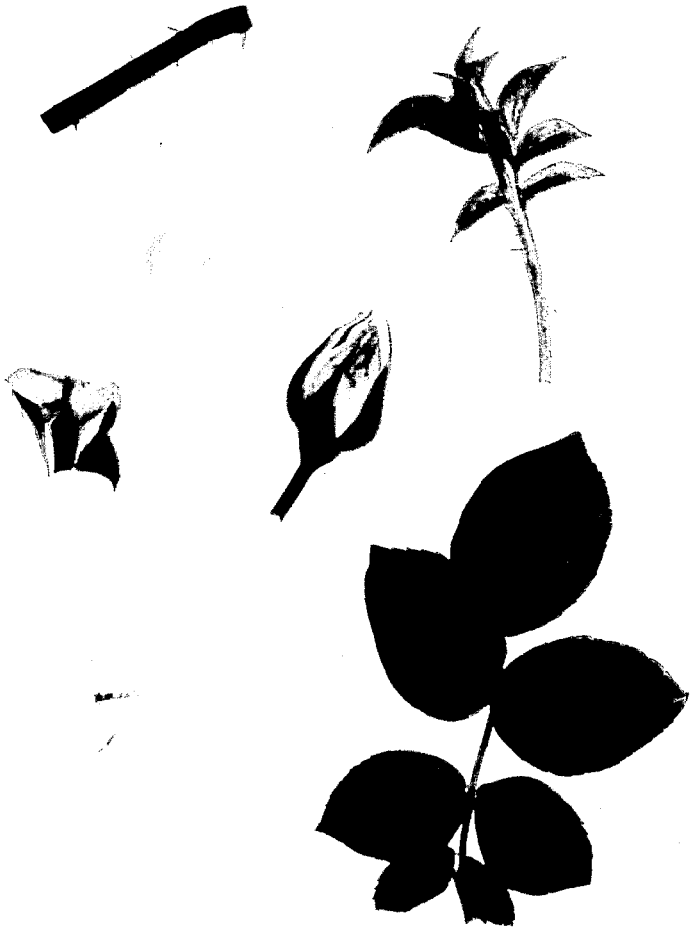
Inventor.
Dennison H. Morey, Jr
By: Robb & Robb
Attorneys.

United States Patent Office

Plant Pat. 2,097
Patented Oct. 3, 1961

2,097
ROSE PLANT

Dennison H. Morey, Jr., Pleasanton, Calif., assignor to Jackson & Perkins Company, Newark, N.Y., a corporation of New York Filed Nov. 25, 1960, Ser. No. 71,851
1 Claim. (Cl. 47—61)

The present invention relates to a new and distinct variety of rose plant of the hybrid tea class, which was originated by me by crossing the variety "Peace" (Plant Patent No. 591) with the variety "Sutter's Gold" (Plant Patent No. 885).

The primary objective of this breeding was to produce a new rose variety comparable to "Peace," but having a wider range of color in the flowers thereof. This objective was fully achieved, along with other desirable improvements, as evidenced by the following unique combination of characteristics which are outstanding in the new variety and which distinguish it from its parents, as well as from all other varieties of which I am aware:

(1) A habit of growth and foliage which resembles those of the variety "Peace," but with the plants being not quite as tall as those of that variety;

(2) A free blooming habit;

(3) Quick recurrence of the blooms; and (4) A distinctive and attractive Empire Yellow general color tonality of the flowers, with the upper half of the petals being Martius Yellow in color and the flowers being lightly overcast with Shrimp Pink on the outer edges of the petals.

Asexual reproduction of the new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Peace."
*Pollen parent.*—"Sutter's Gold."
Classification:
*Botanic.*—Hybrid tea.
*Commercial.*—Hybrid tea.

*Flower*

(Observations made from specimens grown outdoors at Newark, New York, in the early morning during the latter part of the month of August.)

Blooming habit: Recurrent—continuous.
Bud:
*Size.*—Large.
*Form.*—Ovoid; is not affected by wet or hot weather.
*Color.*—When sepals first divide—Brazil Red, Plate 1. When petals begin to unfurl—Pinard Yellow, Plate 4, with outer edges of petals Zinc Orange, Plate 15. When half-blown: inside of petals—Pale Orange-Yellow, Plate 3, with outer edges of petals overcast with Capucine Buff, Plate 3; reverse of petals—Pinard Yellow, Plate 4, with outer edges of petals lightly overcast with Ochraceous-Buff, Plate 15.
*Sepals.*—Serrated; branched; curl back when petals begin to unfurl. Color: inside—Absinthe Green, Plate 31; outside—Spinach Green, Plate 5.

*Calyx.* — Color — Lettuce Green, Plate 5. Shape—apple. Size — small. Aspect — smooth. Odor when rubbed—none.
*Peduncle.* — Length — medium. Aspect — rough. Strength—erect; slender. Color—Lettuce Green, Plate 5.
*Opening.*—Opens up well; is not affected by adverse weather conditions.
Bloom:
*Size.*—Large. Average size when fully expanded—4¼ inches.
*Borne.*—Singly.
*Stems.*—Medium length; normal strength.
*Form (when first open).*—Open. Permanence—retains its form to the end.
*Petalage.*—Double (full but open center). Number of petals under normal conditions—from 35 to 40.
*Color.*—Center of flower—Empire Yellow, Plate 4, with outer edges of petals lightly overcast with La France Pink, Plate 1. Outer petals—Pinard Yellow, Plate 4, with upper half of petals overcast with Shrimp Pink, Plate 1. Base of petals (aiglet)—Light Cadmium, Plate 4. Inside of petals—Empire Yellow, Plate 4, with upper half of petals Martius Yellow, Plate 4 and lightly overcast with Shrimp Pink, Plate 1, on the outer edges of the petals. Reverse of petals—Straw Yellow, Plate 16, with outer edges of petals lightly overcast with Light Orange-Yellow, Plate 3. General tonality from a distance—Empire Yellow, Plate 4, lightly overcast with Shrimp Pink, Plate 1.
*Discoloration.*—General tonality at end of first day—Empire Yellow, Plate 4, with upper half of petals Martius Yellow, Plate 4 and lightly overcast with Shrimp Pink, Plate 1, on the outer edges of the petals. Second day—Empire Yellow, Plate 4, with upper half of petals Martius Yellow, Plate 4 and lightly overcast with Shrimp Pink, Plate 1 on the outer edges of the petals. Third day—Martius Yellow, Plate 4, lightly overcast with Shrimp Pink, Plate 1 on the outer edges of the petals.
Petals:
*Texture.* — Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Strong. Nature—very sweet; tea (average hybrid tea scent).
*Lasting quality.* — On the plant — long. As cut flower—long.

*Genital organs*

Stamens, anthers: Medium size; many; regularly arranged around styles. Color—Buff Yellow, Plate 4.
Stamens, filaments (threads): Medium length. Color—Eugenia Red, Plate 13.
Pollen: Color—Maize Yellow, Plate 4.
Styles: Bunched; uneven length; medium length; thin.
Stigmas: Color—Straw Yellow, Plate 16.
Ovaries: All enclosed in calyx.
Hips: None.
Seeds: None.

*Plant*

Form: Bush.
Growth: Vigorous; upright.
Foliage: Compound of 3–5 leaflets.

*Size.*—Large.

*Quantity.*—Abundant.

*Color.*—New foliage: upper side — Yellowish Oil Green, Plate 5, with serrations Carmine, Plate 1; under side—Lettuce Green, Plate 5, lightly overcast with Carmine, Plate 1. Old foliage: upper side—Varley's Green, Plate 18; under side—Light Bice Green, Plate 17.

*Shape.*—Oval pointed.

*Texture.*—Upper side — leathery; glossy. Under side—smooth.

*Ribs and veins.*—Ordinary.

*Edge.*—Serrated (saw-toothed).

*Serration.*—Both double and single; small.

*Leaf stem.* — Color — light Cress Green, Plate 31. Underside—prickly.

*Stipules.*—Medium length; smooth.

Wood:

*New wood.*—Color—Lettuce Green, Plate 5, lightly overcast with Eugenia Red, Plate 13. Bark—smooth.

*Old wood.*—Color—Forest Green, Plate 17. Bark—smooth.

Thorns:

*Thorns.*—Quantity: on main stalks from base—ordinary; on laterals from stalk—ordinary. Form—flat base; medium length; hooked downward. Color (when young)—Eugenia Red, Plate 13. position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a habit of growth and foliage generally resembling those of the variety "Peace" (Plant Patent No. 591), but with the plants being not as tall as those of the variety "Peace," a free blooming habit, quick recurrence of bloom, and a distinctive Empire Yellow general color tonality of the flowers, with the upper half of the flower petals being Martius Yellow and being lightly overcast with Shrimp Pink on the outer edges of the petals.

No references cited.